(12) United States Patent
Martinez et al.

(10) Patent No.: US 8,965,541 B2
(45) Date of Patent: Feb. 24, 2015

(54) EXERCISE-INTEGRATED WORKSTATION

(75) Inventors: Anthony E. Martinez, St. Agustine, FL (US); Vanessa V. Michelini, Boca Raton, FL (US)

(73) Assignee: International Business Machines Corporation, Armonk, NY (US)

( * ) Notice: Subject to any disclaimer, the term of this patent is extended or adjusted under 35 U.S.C. 154(b) by 575 days.

(21) Appl. No.: 13/288,781

(22) Filed: Nov. 3, 2011

(65) Prior Publication Data

US 2013/0116092 A1    May 9, 2013

(51) Int. Cl.
| | |
|---|---|
| A63B 71/00 | (2006.01) |
| A63B 24/00 | (2006.01) |
| A63B 71/06 | (2006.01) |
| G06F 19/00 | (2011.01) |
| A63B 22/02 | (2006.01) |
| A63B 22/00 | (2006.01) |
| A63B 22/06 | (2006.01) |

(52) U.S. Cl.
CPC ......... *A63B 24/0075* (2013.01); *A63B 71/0619* (2013.01); *A63B 24/0062* (2013.01); *A63B 24/0087* (2013.01); *G06F 19/3481* (2013.01); *A63B 22/02* (2013.01); *A63B 22/0048* (2013.01); *A63B 22/0664* (2013.01); *A63B 2024/0068* (2013.01); *A63B 2024/0078* (2013.01); *A63B 2024/0093* (2013.01); *A63B 2220/10* (2013.01); *A63B 2225/20* (2013.01); *A63B 2225/50* (2013.01); *A63B 2230/75* (2013.01)
USPC ............................................... 700/90; 482/9

(58) Field of Classification Search
None
See application file for complete search history.

(56) References Cited

U.S. PATENT DOCUMENTS

| | | | | |
|---|---|---|---|---|
| 6,746,371 | B1* | 6/2004 | Brown et al. | 482/8 |
| 2002/0083025 | A1* | 6/2002 | Robarts et al. | 706/12 |
| 2005/0108091 | A1* | 5/2005 | Sotak et al. | 705/14 |
| 2006/0097557 | A1 | 5/2006 | Tholkes et al. | |
| 2007/0265139 | A1* | 11/2007 | Glick | 482/8 |
| 2008/0077620 | A1* | 3/2008 | Gilley et al. | 707/104.1 |
| 2008/0255794 | A1 | 10/2008 | Levine | |
| 2008/0300914 | A1* | 12/2008 | Karkanias et al. | 705/2 |
| 2011/0281249 | A1* | 11/2011 | Gammell et al. | 434/247 |
| 2012/0179772 | A1* | 7/2012 | Hinnebusch | 709/213 |
| 2012/0196256 | A1* | 8/2012 | Maeueler et al. | 434/247 |
| 2012/0258433 | A1* | 10/2012 | Hope et al. | 434/247 |

(Continued)

OTHER PUBLICATIONS

Anonymous "Method and System for Presence and Activity Aware Event Dispatching" IPCOM000195732D ip.com May 13, 2010.*

(Continued)

*Primary Examiner* — Ryan Jarrett
(74) *Attorney, Agent, or Firm* — Anna L. Linne; Yee & Associates, PC.; Matthew H. Chung

(57) ABSTRACT

A method, a computer program product, and a computer system initiate an exercise sequence on an exercise-integrated workstation. A set of active monitored activities is identified. A set of preferences and goals for the exercise sequence is identified. A set of accumulated details regarding any user modifications to previous exercise sequences is identified. A set of scheduled events is identified. Responsive to identifying the set of active monitored activities, the set of preferences and goals, the set of accumulated details, and the set of scheduled events, the method determines whether to initiate an exercise sequence. Responsive to determining to initiate the exercise sequence, the method initiates the exercise sequence.

8 Claims, 7 Drawing Sheets

(56) References Cited

U.S. PATENT DOCUMENTS

2013/0218309 A1* 8/2013 Napolitano ................ 700/91
2013/0331993 A1* 12/2013 Detsch et al. .............. 700/275

OTHER PUBLICATIONS

IBM "Software system for facilitating incidental exercise on the job" IPCOM000190089D ip.com Nov. 17, 2009.*

Amazon.com, FitDesk Pro, retrieved from http://www.amazon.com/New-FitDesk-Pro-Indoor-Laptop/dp/B004L1AJFA on Jun. 9, 2011, 6 pages.

Mayo Clinic, "Office of the Future" Environment Study, retrieved from http://www.mayoclinic.org/news2008-rst/4924.html on Jun. 9, 2011, 2 pages.

Steelcase Store, Walkstations by Details, "Walkstation," retrieved from www.steelcase.com on Jun. 9, 2011, 3 pages.

Steelcase Store, Walkstations by Details, "Sit-to-Walkstation," retrieved from www.steelcase.com on Jun. 9, 2011, 3 pages.

* cited by examiner

FIG. 2
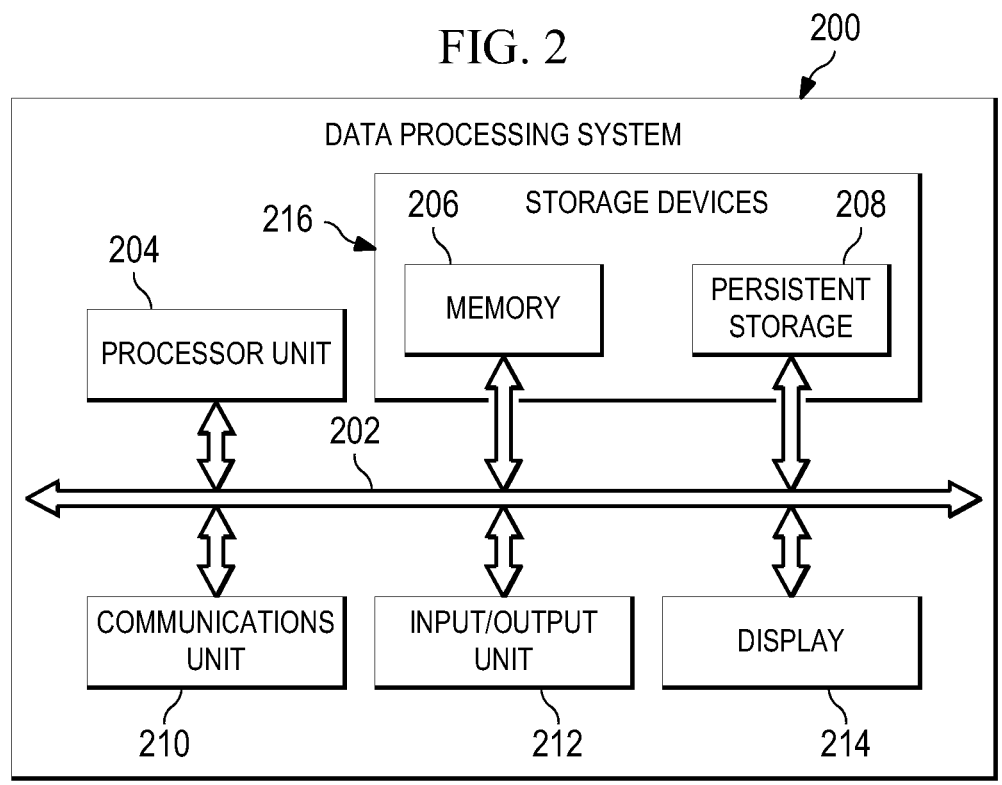
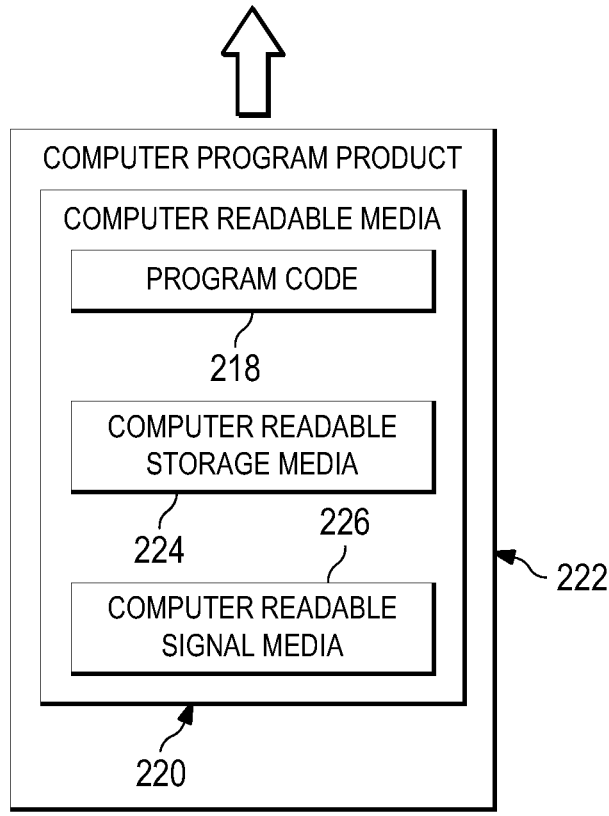

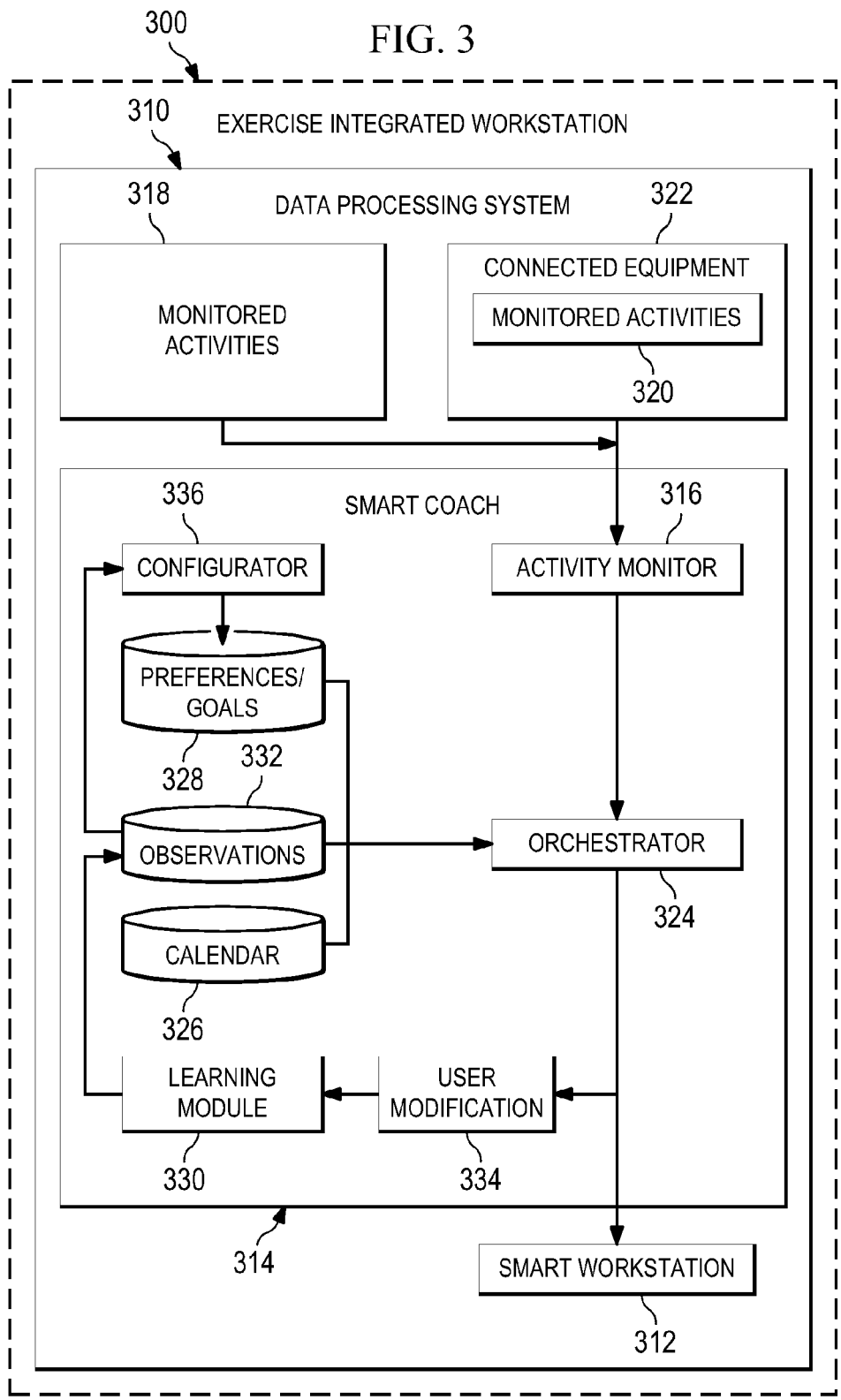

DATA STRUCTURE 400

| MONITORED ACTIVITIES 410 | EXERCISE DESIGNATION 412 | INTENSITY DESIGNATION 414 |
|---|---|---|
| APPLICATION | EXERCISE ALLOWED? | INTENSITY |
| LOTUS NOTES | YES | HIGH |
| ADOBE PHOTOSHOP | NO | -- |
| MICROSOFT EXCEL | YES | LOW |
| LOTUS SYMPHONY | YES | MEDIUM |

FIG. 4

DATA STRUCTURE 500

| DEVICES 510 | EXERCISE DESIGNATION 512 | INTENSITY DESIGNATION 514 |
|---|---|---|
| DEVICE | EXERCISE ALLOWED? | INTENSITY |
| KEYBOARD | YES | HIGH |
| MOUSE | YES | MEDIUM |
| USB TELEPHONE | YES | HIGH |
| GRAPHICS TABLET | NO | -- |
| TRACKPAD | YES | LOW |

FIG. 5

EXERCISE-INTEGRATED WORKSTATION

BACKGROUND

1. Field

The disclosure relates generally to a computer implemented method, a computer program product, and a data processing system. More specifically, the disclosure relates to a computer implemented method, a computer program product, and a data processing system for providing an exercise-integrated workstation.

2. Description of the Related Art

A fitness craze has recently swept the United States and other countries. From fat-free potato chips to treadmills, people around the world have become obsessed with weight loss and healthy living. Accordingly, record numbers of new fitness products/exercise equipment from multiple manufacturers have emerged to meet this obsession (including stair climbers, treadmills, recumbent bicycles, ski machines, rowing machines, weight lifting machines, and the like).

Many pieces of exercise equipment, when utilized regularly, are very useful for weight loss, for improving cardiovascular endurance, and for strengthening various muscles. Most exercise equipment includes a monitoring device that may include a pulse monitor, a distance meter, a rate monitor, a time monitor, a strain gauge, an accelerometer and/or any other sensor for measuring the physical activity/performance level of a user on the equipment. Moreover, monitoring devices typically request personal data from the user such as age, weight, and desired physical fitness level. The monitoring device utilizes the personal data in combination with a level of physical exertion and heart rate to estimate calories burned, fitness levels achieved, and other fitness related data. In addition, the monitor may adjust the resistance or speed of a piece of exercise equipment in order to aid the user in reaching and/or maintaining a fitness level for that exercise session.

However, whether due to busy schedules, lack of discipline, or just plain laziness, many people who interact with computers and telephones at a workstation fail to engage in a regular exercise sequence for maintaining good health. There are existing mechanisms that encourage people to exercise and most of these are triggered primarily via some type of audio/visual reminder. These mechanisms are not always effective because it is often impossible or inconvenient to halt work to begin an exercise sequence without degrading productivity.

SUMMARY

According to one embodiment of the present invention, a method is provided for initiating an exercise sequence on an exercise-integrated workstation. A computer identifies a set of active monitored activities. The computer identifies a set of preferences and goals for the exercise sequence. The computer identifies a set of accumulated details regarding any user modifications to previous exercise sequences. The computer identifies a set of scheduled events. Responsive to identifying the set of active monitored activities, the set of preferences and goals, the set of accumulated details, and the set of scheduled events, the computer determines whether to initiate an exercise sequence. Responsive to determining to initiate the exercise sequence, the computer initiates the exercise sequence.

According to another embodiment of the present invention, a computer program product is provided for initiating an exercise sequence on an exercise-integrated workstation. The computer program product comprises one or more computer-readable, tangible storage devices. Program instructions, stored on at least one of the one or more storage devices, identify a set of active monitored activities. Program instructions, stored on at least one of the one or more storage devices, identify a set of preferences and goals for the exercise sequence. Program instructions, stored on at least one of the one or more storage devices, identify a set of accumulated details regarding any user modifications to previous exercise sequences. Program instructions, stored on at least one of the one or more storage devices, to identify a set of scheduled events. Program instructions, stored on at least one of the one or more storage devices, responsive to identifying the set of active monitored activities, the set of preferences and goals, the set of accumulated details, and the set of scheduled events, determine whether to initiate an exercise sequence. Program instructions, stored on at least one of the one or more storage devices, responsive to determining to initiate the exercise sequence, initiate the exercise sequence.

According to one embodiment of the present invention, a computer system is provided for initiating an exercise sequence on an exercise-integrated workstation. The computer system comprises one or more processors, one or more computer-readable memories and one or more computer-readable, tangible storage devices. Program instructions, stored on at least one of the one or more storage devices, identify a set of active monitored activities. Program instructions, stored on at least one of the one or more storage devices, identify a set of preferences and goals for the exercise sequence. Program instructions, stored on at least one of the one or more storage devices, identify a set of accumulated details regarding any user modifications to previous exercise sequences. Program instructions, stored on at least one of the one or more storage devices, to identify a set of scheduled events. Program instructions, stored on at least one of the one or more storage devices, responsive to identifying the set of active monitored activities, the set of preferences and goals, the set of accumulated details, and the set of scheduled events, determine whether to initiate an exercise sequence. Program instructions, stored on at least one of the one or more storage devices, responsive to determining to initiate the exercise sequence, initiate the exercise sequence.

BRIEF DESCRIPTION OF THE SEVERAL VIEWS OF THE DRAWINGS

FIG. 2 is an illustration of a data processing system in accordance with an advantageous embodiment;

FIG. 3 is an exercise-integrated workstation according to an illustrative embodiment;

FIG. 4 is a data structure showing monitored applications according to an illustrative embodiment;

FIG. 5 is a data structure showing monitored input devices according to an illustrative embodiment;

DETAILED DESCRIPTION

Figure 1:
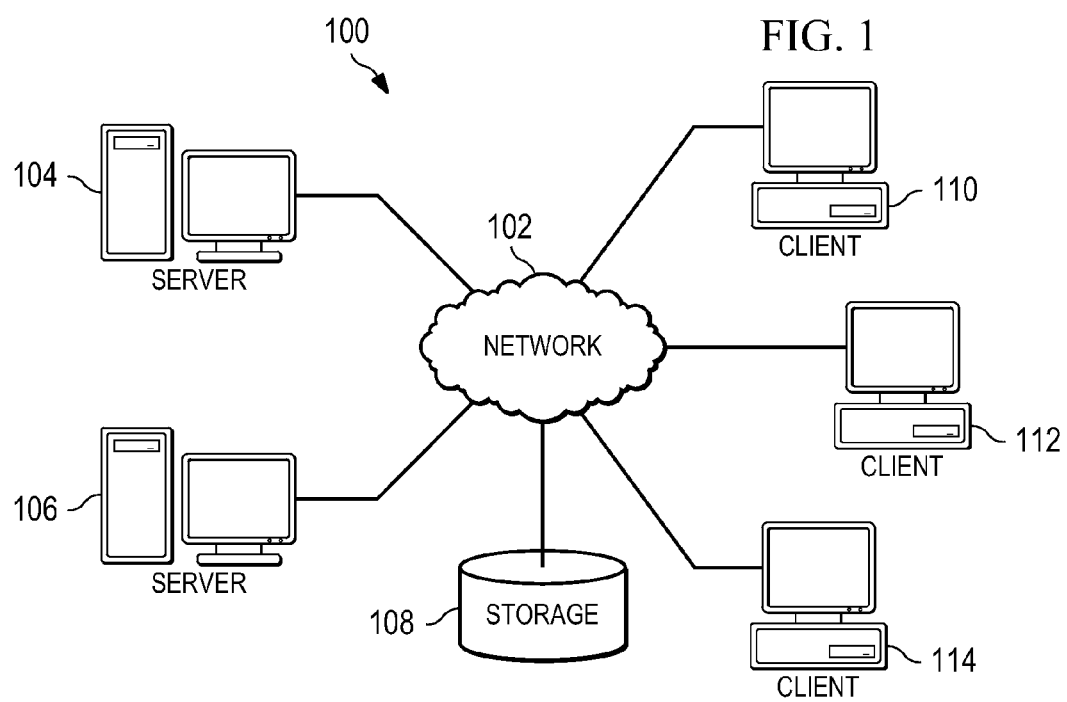
FIG. 1 depicts a pictorial representation of a network of data processing systems in which illustrative embodiments may be implemented.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

With reference now to the figures and, in particular, with reference to FIG. 1, an illustrative diagram of a data processing environment is provided in which illustrative embodiments may be implemented. It should be appreciated that FIG. 1 is only provided as an illustration of one implementation and is not intended to imply any limitation with regard to the environments in which different embodiments may be implemented. Many modifications to the depicted environments may be made.

FIG. 1 depicts a pictorial representation of a network of data processing systems in which illustrative embodiments may be implemented. Network data processing system 100 is a network of computers in which the illustrative embodiments may be implemented. Network data processing system 100 contains network 102, which is the medium used to provide communications links between various devices and computers connected together within network data processing system 100. Network 102 may include connections, such as wire, wireless communication links, or fiber optic cables.

In the depicted example, server computer 104 and server computer 106 connect to network 102 along with storage unit 108. In addition, client computers 110, 112, and 114 connect to network 102. Client computers 110, 112, and 114 may be, for example, personal computers or network computers. In the depicted example, server computer 104 provides information, such as boot files, operating system images, and applications to client computers 110, 112, and 114. Client computers 110, 112, and 114 are clients to server computer 104 in this example. Network data processing system 100 may include additional server computers, client computers, and other devices not shown.

Program code located in network data processing system 100 may be stored on a computer recordable storage medium and downloaded to a data processing system or other device for use. For example, program code may be stored on a computer recordable storage medium on server computer 104 and downloaded to client computer 110 over network 102 for use on client computer 110.

In the depicted example, network data processing system 100 is the Internet with network 102 representing a worldwide collection of networks and gateways that use the Transmission Control Protocol/Internet Protocol (TCP/IP) suite of protocols to communicate with one another. At the heart of the Internet is a backbone of high-speed data communication lines between major nodes or host computers consisting of thousands of commercial, governmental, educational and other computer systems that route data and messages. Of course, network data processing system 100 also may be implemented as a number of different types of networks, such as, for example, an intranet, a local area network (LAN), or a wide area network (WAN). FIG. 1 is intended as an example, and not as an architectural limitation for the different illustrative embodiments.

Turning now to FIG. 2, an illustration of a data processing system is depicted in accordance with an advantageous embodiment. In this illustrative example, data processing system 200 includes communications framework 202, which provides communications between processor unit 204, memory 206, persistent storage 208, communications unit 210, input/output (I/O) unit 212, and display 214.

Processor unit 204 serves to execute instructions for software that may be loaded into memory 206. Processor unit 204 may be a number of processors, a multi-processor core, or some other type of processor, depending on the particular implementation. A number, as used herein with reference to an item, means one or more items. Further, processor unit 204 may be implemented using a number of heterogeneous processor systems in which a main processor is present with secondary processors on a single chip. As another illustrative example, processor unit 204 may be a symmetric multi-processor system containing multiple processors of the same type.

Memory 206 and persistent storage 208 are examples of storage devices 216. A storage device is any piece of hardware that is capable of storing information, such as, for example, without limitation, data, program code in functional form, and/or other suitable information either on a temporary basis and/or a permanent basis. Storage devices 216 may also be referred to as computer readable storage devices in these examples. Memory 206, in these examples, may be, for example, a random access memory or any other suitable volatile or non-volatile storage device. Persistent storage 208 may take various forms, depending on the particular implementation.

For example, persistent storage 208 may contain one or more components or devices. For example, persistent storage 208 may be a hard drive, a flash memory, a rewritable optical disk, a rewritable magnetic tape, or some combination of the above. The media used by persistent storage 208 also may be removable. For example, a removable hard drive may be used for persistent storage 208.

Communications unit 210, in these examples, provides for communications with other data processing systems or devices. In these examples, communications unit 210 is a network interface card. Communications unit 210 may provide communications through the use of either or both physical and wireless communications links.

Input/output unit 212 allows for input and output of data with other devices that may be connected to data processing system 200. For example, input/output unit 212 may provide a connection for user input through a keyboard, a mouse, and/or some other suitable input device. Further, input/output unit 212 may send output to a printer. Display 214 provides a mechanism to display information to a user.

Instructions for the operating system, applications, and/or programs may be located in storage devices 216, which are in communication with processor unit 204 through communications framework 202. In these illustrative examples, the instructions are in a functional form on persistent storage 208. These instructions may be loaded into memory 206 for execution by processor unit 204. The processes of the different embodiments may be performed by processor unit 204 using computer implemented instructions, which may be located in a memory, such as memory 206.

These instructions are referred to as program code, computer usable program code, or computer readable program code that may be read and executed by a processor in processor unit 204. The program code in the different embodiments may be embodied on different physical or computer readable storage media, such as memory 206 or persistent storage 208.

Program code 218 is located in a functional form on computer readable media 220 that is selectively removable and may be loaded onto or transferred to data processing system 200 for execution by processor unit 204. Program code 218 and computer readable media 220 form computer program product 222 in these examples. In one example, computer readable media 220 may be computer readable storage media 224 or computer readable signal media 226. Computer readable storage media 224 may include, for example, an optical or magnetic disk that is inserted or placed into a drive or other device that is part of persistent storage 208 for transfer onto a storage device, such as a hard drive, that is part of persistent storage 208. Computer readable storage media 224 also may take the form of a persistent storage, such as a hard drive, a thumb drive, or a flash memory, that is connected to data processing system 200. In some instances, computer readable storage media 224 may not be removable from data processing system 200. In these examples, computer readable storage media 224 is a physical or tangible storage device used to store program code 218 rather than a medium that propagates or transmits program code 218. Computer readable storage media 224 is also referred to as a computer readable tangible storage device or a computer readable physical storage device. In other words, computer readable storage media 224 is a media that can be touched by a person.

Alternatively, program code 218 may be transferred to data processing system 200 using computer readable signal media 226. Computer readable signal media 226 may be, for example, a propagated data signal containing program code 218. For example, computer readable signal media 226 may be an electromagnetic signal, an optical signal, and/or any other suitable type of signal. These signals may be transmitted over communications links, such as wireless communications links, optical fiber cable, coaxial cable, a wire, and/or any other suitable type of communications link. In other words, the communications link and/or the connection may be physical or wireless in the illustrative examples.

In some advantageous embodiments, program code 218 may be downloaded over a network to persistent storage 208 from another device or data processing system through computer readable signal media 226 for use within data processing system 200. For instance, program code stored in a computer readable storage medium in a server data processing system may be downloaded over a network from the server to data processing system 200. The data processing system providing program code 218 may be a server computer, a client computer, or some other device capable of storing and transmitting program code 218.

The different components illustrated for data processing system 200 are not meant to provide architectural limitations to the manner in which different embodiments may be implemented. The different advantageous embodiments may be implemented in a data processing system including components in addition to or in place of those illustrated for data processing system 200. Other components shown in FIG. 2 can be varied from the illustrative examples shown. The different embodiments may be implemented using any hardware device or system capable of running program code. As one example, the data processing system may include organic components integrated with inorganic components and/or may be comprised entirely of organic components excluding a human being. For example, a storage device may be comprised of an organic semiconductor.

In another illustrative example, processor unit 204 may take the form of a hardware unit that has circuits that are manufactured or configured for a particular use. This type of hardware may perform operations without needing program code to be loaded into a memory from a storage device to be configured to perform the operations.

For example, when processor unit 204 takes the form of a hardware unit, processor unit 204 may be a circuit system, an application specific integrated circuit (ASIC), a programmable logic device, or some other suitable type of hardware configured to perform a number of operations. With a programmable logic device, the device is configured to perform the number of operations. The device may be reconfigured at a later time or may be permanently configured to perform the number of operations. Examples of programmable logic devices include, for example, a programmable logic array, a programmable array logic, a field programmable logic array, a field programmable gate array, and other suitable hardware devices. With this type of implementation, program code 218 may be omitted because the processes for the different embodiments are implemented in a hardware unit.

In still another illustrative example, processor unit 204 may be implemented using a combination of processors found in computers and hardware units. Processor unit 204 may have a number of hardware units and a number of processors that are configured to run program code 218. With this depicted example, some of the processes may be implemented in the number of hardware units, while other processes may be implemented in the number of processors.

In another example, a bus system may be used to implement communications framework 202 and may be comprised of one or more buses, such as a system bus or an input/output bus. Of course, the bus system may be implemented using any suitable type of architecture that provides for a transfer of data between different components or devices attached to the bus system.

Additionally, a communications unit may include a number of more devices that transmit data, receive data, or transmit and receive data. A communications unit may be, for example, a modem or a network adapter, two network adapters, or some combination thereof. Further, a memory may be, for example, memory 206, or a cache, such as found in an interface and memory controller hub that may be present in communications framework 202.

The illustrative embodiments herein provide a computer implemented method, a data processing system, and a computer program product for adjustably determining carrier selection based on variable volumetric weight and variable completion times. A product is identified for production. The product for production has a variable weight and a variable dimension based on components included in the product for production. A projected volumetric weight of the product for production is determined. A projected completion time of the product for production is determined. A projected carrier assignment of the product for production is then determined in response to determining the projected volumetric weight of the product for production and determining the projected completion time of the product for production.

Referring now to FIG. 3, an exercise-integrated workstation is shown according to an illustrative embodiment. Exercise-integrated workstation 300 includes data processing system 310, and smart workstation 312. Data processing system 310 is a data processing system such as data processing system 200 of FIG. 2.

Data processing system 310 executes smart coach 314. Smart coach 314 is a software application that determines optimal times for exercise throughout a work day and schedules the execution of those optimal times for exercise on smart workstation 312.

Smart coach 314 includes activity monitor 316. Activity monitor 316 is a software component that observes monitored activities 318 executing on data processing system 310, as well as monitored activities 320 occurring on connected equipment 322. Monitored activities 318 can be, for example, the execution of certain software applications on data processing system 310, such as for example, but not limited to, an email application, a photo editing application, a spreadsheet application, and a word processing application. Additionally, monitored activities 318 can be, for example, the use of certain data input devices for data processing system 310, such as for example, but not limited to, a keyboard, a mouse, a graphics tablet, and a trackpad. Monitored activities 320 can be for example, but not limited to, the use of a peripheral component connected to data processing system 310, such as for example, but not limited to, a universal serial bus connected telephone. Activity monitor 316 informs the orchestrator as to the current state of monitored activities 318 and monitored activities 320.

Orchestrator 324 is a software component that determines when to initiate an exercise sequence on smart workstation 312. Orchestrator 324 determines when to initiate an exercise sequence based on inputs from smart coach 314, including but not limited to, a current state of monitored activities 318 and monitored activities 320, calendared events recorded in calendar 326, user goals and preferences recorded in preferences/goals 328, and historical observations gathered by learning module 330 and recorded in observations 332.

Calendar 326 is a data structure, such as a database, that contains scheduled events. For example, the scheduled events may be, but not limited to, an upcoming teleconference or video conference, a meeting, or scheduled time during which a user will be away from smart workstation 312. In one illustrative embodiment, calendar 326 is not a core component of smart coach 314, but is rather a separate calendar application with which smart coach 314 can interface to retrieve scheduled events. For example, calendar 326 may be implemented as part of a separate calendar application such as, for example, but not limited to, IBM Lotus Notes®, Google Calendar®, Microsoft Outlook®, and Apple iCal® (IBM LOTUS NOTES is a trademark of IBM Corp. in the United States, other countries, or both; GOOGLE CALENDAR is a trademark of Google, Inc. in the United States, other countries, or both; MICROSOFT OUTLOOK is a trademark of Microsoft, Inc. in the United States, other countries, or both; and APPLE ICAL is a trademark of Apple, Inc. in the United States, other countries, or both).

Preferences/goals 328 is a data structure, such as a database, that contains user specifications about the desired exercise goals. These specifications can be, for example but not limited to, goals regarding a specific number of calories to burn during an exercise session or over a period of time, goals regarding an amount of time to exercise during an exercise session or over a period of time, goals regarding an amount of weight to lose or gain over a period of time, and goals regarding a desired target body mass index.

Preferences/goals 328 further contains user specifications regarding what calendar events and monitored activities are compatible with an exercise sequence initiated by orchestrator 324. For example, a morning teleconference may be acceptable to a user for an exercise sequence, however, an afternoon teleconference may not be acceptable to the user. Additionally, preferences/goals 328 may include user specified exercise intensity for a specific one of monitored activities 318, monitored activities 320, or for a specific calendared event listed in calendar 326.

In an illustrative embodiment, preferences/goals 328 may contain an indication of which monitored activities 318 and 320 are compatible with an exercise sequence. For example, monitored activities such as an email client, a web browser, or an instant messaging client might be indicated as being compatible with an exercise sequence, while video conferencing, image editing, or video presentations might be indicated as not being compatible with an exercise sequence.

In an illustrative embodiment, preferences/goals 328 may contain an indication of certain times at which an exercise sequence should not be initiated. For example, times such as early afternoons (i.e., soon after lunch), early mornings, or weekends might be indicated as times during which an exercise sequence should not be initiated. Furthermore, preferences/goals 328 may contain an indication of certain calendared events within calendar 326 that are incompatible with an exercise sequence. For example, calendared events such as online training sessions, online conferences, and scheduled meetings with key employees or clients might be indicated as times during which an exercise sequence should not be initiated.

In an illustrative embodiment, preferences/goals 328 may contain an indication of a user's exercise goals that should be achieved over given period of time. For example, a user's exercise goals may indicate a desire to exercise for a predetermined number of minutes per day, a predetermined number of hours per week, or a predetermined number of hours per month. As a further example, a user's exercise goals may indicate a desire to burn a certain number of calories per day, a certain number of calories per week, or a certain number of calories per month.

In an illustrative embodiment, preferences/goals 328 may contain an indication of a user's specific exercise needs. For example, a user's specific exercise needs may include an indication of a maximum exercise intensity that should not be exceeded, an indication of a maximum exercise duration that should not be exceeded, or an indication of any medically prescribed exercise restrictions that are specific to the user.

Observations 332 is a data structure, such as a database, that contains accumulated details from learning module 330 regarding any user modifications to exercise events initiated by orchestrator 324. User modifications contained within observations 332 detail any override actions taken by the user either prior to, or during an exercise sequence. Accumulated details contained within observations 332 can include, but are not limited to, applications running at the time of the modification, peripheral and input devices in use at the time of the user modification, and calendar events occurring at the time of the user modification. Accumulated details contained within observations 332 can also include any rationale that the user has provided for modifying the exercise sequence. Override actions taken by the user can include, but are not limited to, a cancellation of the exercise sequence, a delay of the exercise sequence, a modification of the intensity of the exercise sequence, and a modification of the duration of the exercise sequence. In an illustrative embodiment, the user can also initiate an unscheduled user-initiated exercise sequence. Details regarding the state of smart workstation 312 when unscheduled user-initiated exercise sequence is initiated are stored as observations 332.

Learning module 330 is a software component that records state information and proffered explanations regarding user modifications to exercise events. When a user makes a user modification 334 to exercise events initiated by orchestrator 324, learning module 330 logs the current state of data processing system 310, including which of monitored activities 318 are currently active. Learning module 330 records any logged information into observations 332.

Configurator 336 is a software module that maintains preferences/goals 328. Through a dialog with the user, configurator 336 receives user specifications regarding what calendar events and monitored activities are compatible with an exercise sequence initiated by orchestrator 324. Configurator 336 then stores those user specifications in preferences/goals 328.

Referring now to FIG. 4, a data structure showing monitored activities is shown according to an illustrative embodiment. The monitored activities can be, for example, monitored activities 318 of FIG. 3. Data structure 400 can be a data structure that indicates which of monitored activities is compatible with an exercise sequence, such as preferences/goals 328 of FIG. 3.

Data structure 400 includes monitored activities 410. Monitored activities 410 are software applications that can be executed on an exercise-integrated workstation, such as exercise-integrated workstation 300 of FIG. 3. Monitored activities 410 can include, for example, an email application, a photo editing application, a spreadsheet application, and a word processing application.

Data structure 400 includes exercise designation 412. Exercise designation 412 is an indication as to whether exercise is permitted by the user during use of the associated one of monitored activities 410. For example, a user may indicate that monitored activities such as an email client, a web browser, or an instant messaging client might be indicated as being compatible with an exercise sequence, while video conferencing, image editing, or video presentations might be indicated as not being compatible with an exercise sequence. Exercise designation 412 indicates that an email client, a web browser, and an instant messaging client of monitored activities 410 are compatible with an exercise sequence. Exercise designation 412 indicates that a photo editing application of monitored activities 410 is not compatible with an exercise sequence.

Data structure 400 includes intensity designation 414. Intensity designation 414 is an indication as to a user-specified exercise intensity the associated one of monitored activities 410. For example, a user may indicate that an exercise sequence may be more intense during some of monitored activities 410, while exercise sequences during others of monitored activities 410 should be conducted at some lesser intensity. Intensity designation 414 indicates that an exercise sequence can be performed at a high intensity while an email client is running. Intensity designation 414 indicates that an exercise sequence can be performed at a low intensity while a spreadsheet application is running. Intensity designation 414 indicates that an exercise sequence can be performed at a medium intensity while a text editor is running.

Referring now to FIG. 5, a data structure showing monitored input devices is shown according to an illustrative embodiment. The monitored activities can be, for example, monitored activities 318 and monitored activities 320 of FIG. 3. Data structure 500 can be a data structure that indicates which of monitored activities is compatible with an exercise sequence, such as preferences/goals 328 of FIG. 3.

Data structure 500 includes devices 510. Devices 510 are input devices that are utilized to interact with an application executing on an exercise-integrated workstation, such as Exercise-integrated workstation 300 of FIG. 3. Devices 510 can include, for example, a keyboard, a mouse, a universal serial bus telephone, a graphics tablet, and a trackpad.

Data structure 500 includes exercise designation 512. Exercise designation 512 is an indication as to whether exercise is permitted by the user during use of the associated one of devices 510. For example, a user may indicate that monitored activities such as a keyboard, a mouse, a universal serial bus telephone, and a graphics tablet might be indicated as being compatible with an exercise sequence, while a trackpad might be indicated as not being compatible with an exercise sequence. Exercise designation 512 indicates that a keyboard, a mouse, a universal serial bus telephone, and a graphics tablet of devices 510 are compatible with an exercise sequence. Exercise designation 512 indicates that a graphics tablet of devices 510 is not compatible with an exercise sequence.

Data structure 500 includes intensity designation 514. Intensity designation 514 is an indication as to a user-specified exercise intensity the associated one of devices 510. For example, a user may indicate that an exercise sequence may be more intense during use of some of devices 510, while exercise sequences during use of others of devices 510 should be conducted at some lesser intensity. Intensity designation 514 indicates that an exercise sequence can be performed at a high intensity while a keyboard or universal serial bus telephone is in use. Intensity designation 514 indicates that an exercise sequence can be performed at a medium intensity while a mouse is in use. Intensity designation 514 indicates that an exercise sequence can be performed at a low intensity while a trackpad is in use.

Figure 6:
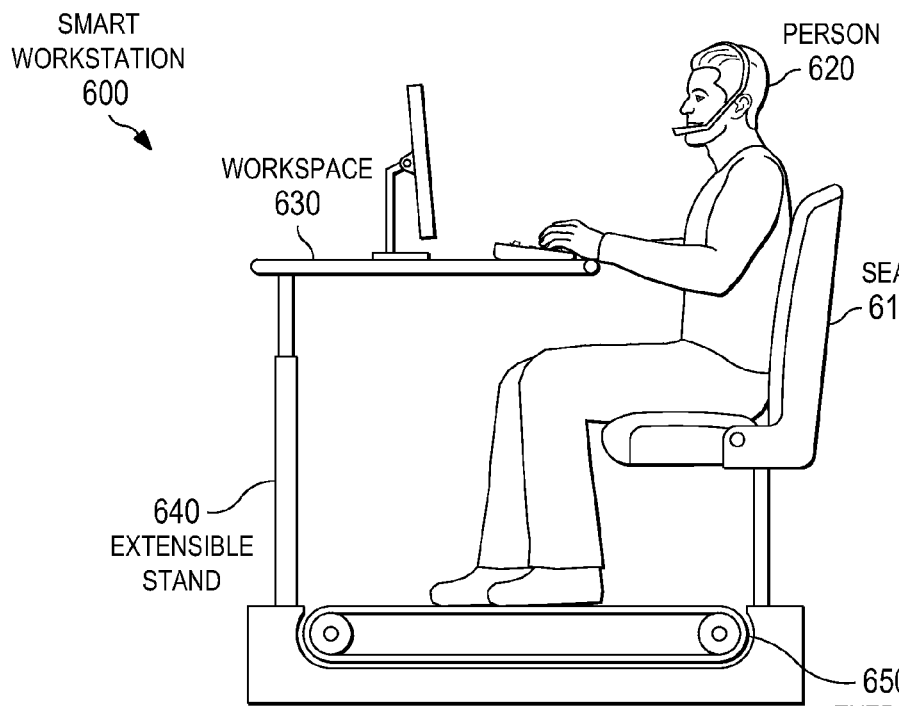
FIG. 6 is a smart workstation in a sedentary state wherein an exercise sequence is not currently being executed according to an illustrative embodiment.

Referring now to FIG. 6, a smart workstation is shown according to an illustrative embodiment. Smart workstation 600 is smart workstation 312 of FIG. 3. Smart workstation 600 is shown in a sedentary state wherein an exercise sequence is not currently being executed.

Smart workstation 600 includes seat 610. Seat 610 provides person 620 with a chair or other support when smart workstation 600 is in a sedentary state. When smart workstation 600 transforms to an active state, due to the execution of an exercise sequence, at least a portion of seat 610 is electromechanically actuated away from person 620 such that seat 610 does not protrude into the area required by person 620 to perform the exercise sequence.

Smart workstation 600 includes workspace 630. Workspace 630 is a desk, table, or other surface that can support user interface devices for a data processing system, such as data processing system 310 of FIG. 3. The user interface devices can be, for example, but not limited to, a monitor, a keyboard, a mouse, a graphics tablet, and a trackpad. When smart workstation 600 transforms from a sedentary state to an active state, due to the execution of an exercise sequence, at least a portion of workspace 630 is electromechanically actuated away from person 620 such that workspace 630 does not protrude into the area required by person 620 to perform the exercise sequence.

Smart workstation 600 includes extensible stand 640. Extensible stand 640 maintains workspace 630 at an ergonomically acceptable height when smart workstation 600 is in a sedentary state and when smart workstation 600 is in an active state. When smart workstation 600 transforms from a sedentary state to an active state due to the execution of an exercise sequence, extensible stand 640 is electromechanically actuated upward such that person 620 is still provided with ergonomically acceptable access to workspace 630.

Smart workstation 600 includes exercise apparatus 650. Exercise apparatus 650 is a treadmill, stair climber, elliptical trainer, or other machinery capable on which person 620 can perform an aerobic exercise. Exercise apparatus 650 is capable of providing a variety of intensities, through an increase in resistance, inclination, speed, or combinations thereof.

Figure 7:
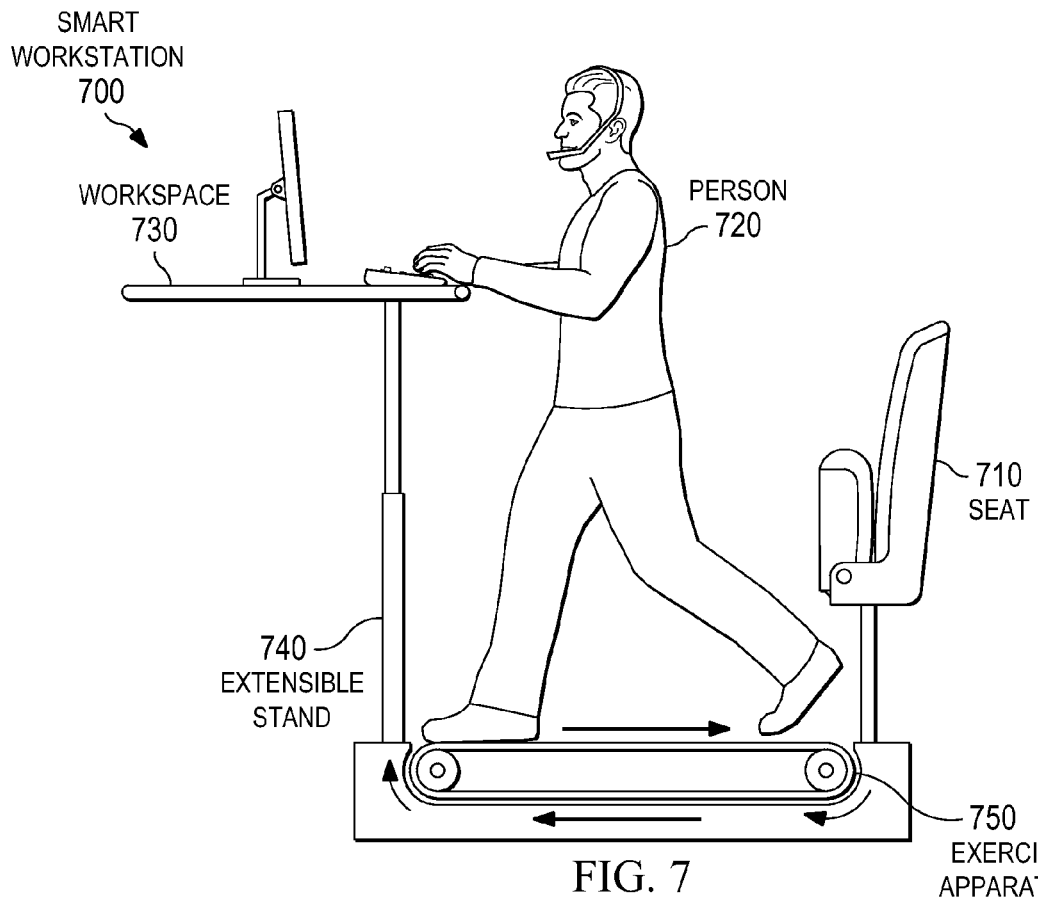
FIG. 7 is a smart workstation shown in an active state wherein an exercise sequence is currently being executed according to an illustrative embodiment.

Referring now to FIG. 7, a smart workstation is shown according to an illustrative embodiment. Smart workstation 700 is smart workstation 312 of FIG. 3. Smart workstation 700 is shown in an active state wherein an exercise sequence is currently being executed.

Smart workstation 700 includes seat 710. Seat 710 is seat 610 of FIG. 6. When smart workstation 700 transforms to an active state, due to the execution of an exercise sequence, at least a portion of seat 710 is electromechanically actuated away from person 720 such that seat 710 does not protrude into the area required by person 720 to perform the exercise sequence.

Smart workstation 700 includes workspace 730. Workspace 730 is workspace 630 of FIG. 6. When smart workstation 700 transforms from a sedentary state to an active state, due to the execution of an exercise sequence, at least a portion of workspace 730 is electromechanically actuated away from person 720 such that workspace 730 does not protrude into the area required by person 720 to perform the exercise sequence.

Smart workstation 700 includes extensible stand 740. Extensible stand 740 is extensible stand 640 of FIG. 6. When smart workstation 700 transforms from a sedentary state to an active state due to the execution of an exercise sequence, extensible stand 740 is electromechanically actuated upward such that person 720 is still provided with ergonomically acceptable access to workspace 730.

Smart workstation 700 includes exercise apparatus 750. Exercise apparatus 750 is exercise apparatus 650 of FIG. 6. During an exercise sequence, exercise apparatus 750 is capable of providing a variety of intensities, through an increase in resistance, inclination, speed, or combinations thereof.

Figure 8:
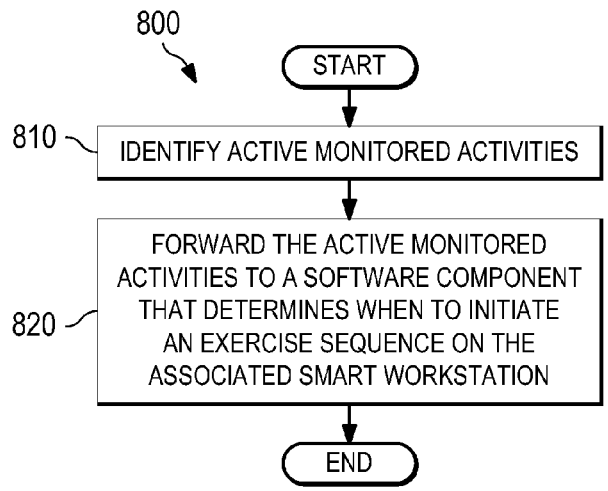
FIG. 8 is a flowchart of processing steps for observing monitored activities executing on a data processing system and monitored activities occurring on connected equipment according to an illustrative embodiment.

Referring now to FIG. 8, a flowchart of processing steps for observing monitored activities executing on a data processing system and monitored activities occurring on connected equipment is shown according to an illustrative embodiment. Process 800 is a software process, executing on a software component, such as activity monitor 316 of FIG. 3.

Process 800 begins by identifying active monitored activities (step 810). Monitored activities can be, for example, the execution of certain software applications on a data processing system, such as for example, but not limited to, an email application, a photo editing application, a spreadsheet application, and a word processing application. Additionally, monitored activities can be, for example, the use of certain data input devices for a data processing system, such as for example, but not limited to, a keyboard, a mouse, a graphics tablet, and a trackpad. Monitored activities can be for example, but not limited to, the use of a peripheral component connected to data processing system, such as for example, but not limited to, a universal serial bus connected telephone. Monitored activities can be monitored activities 318 or monitored activities 320 of FIG. 3. In one illustrative embodiment, process 800 can identify monitored activities by examining state information of the data processing system.

Responsive to identifying active monitored activities, process 800 forwards the active monitored activities to a software component that determines when to initiate an exercise sequence on the associated smart workstation (step 820), such as orchestrator 324, with the process terminating thereafter. Based on the active monitored activities, the orchestrator can then determine whether an exercise sequence can be presently initiated.

Figure 9:
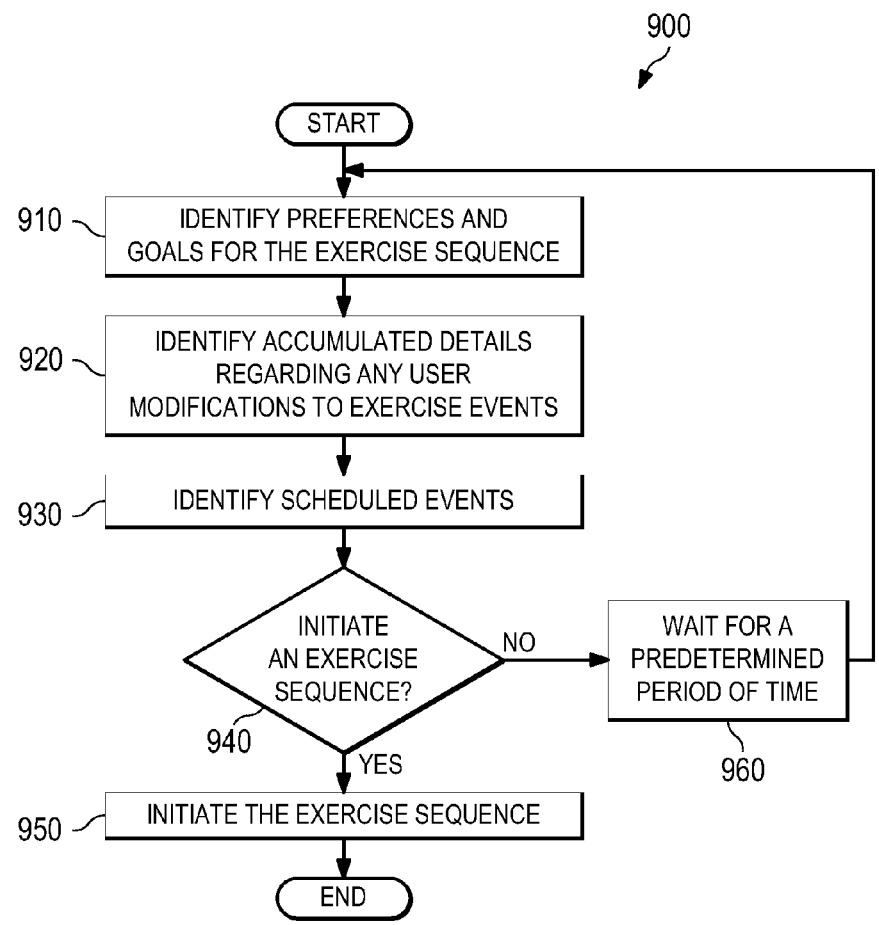
FIG. 9 is a flowchart of processing steps for determining when to initiate an exercise sequence on the associated smart workstation according to an illustrative embodiment.

Referring now to FIG. 9, a flowchart of processing steps for determining when to initiate an exercise sequence on the associated smart workstation is shown according to an illustrative embodiment. Process 800 is a software process, executing on a software component, such as orchestrator 324 of FIG. 3.

Process 900 begins by identifying preferences and goals for the exercise sequence (step 910). The preferences and goals are user specifications about the desired exercise goals. These specifications can be, for example but not limited to, goals regarding a specific number of calories to burn during an exercise session or over a period of time, goals regarding an amount of time to exercise during an exercise session or over a period of time, goals regarding an amount of weight to lose or gain over a period of time, and goals regarding a desired target body mass index. The preferences and goals can be identified from an associated data structure, such as preferences/goals 328 of FIG. 3.

The preferences and goals may include user specifications regarding what calendar events and monitored activities are compatible with an exercise sequence. The preferences and goals may include an indication of which of monitored activities are compatible with an exercise sequence as well as a user specified exercise intensity for a specific one of monitored activity, or for a specific calendared event. The preferences and goals may include an indication of certain times at which an exercise sequence should not be initiated. The preferences and goals may include an indication of certain calendared events that are incompatible with an exercise sequence. The preferences and goals may include an indication of a user's exercise goals that should be achieved over given period of time, for example, a predetermined period of time to exercise, or a desire to burn a certain number of calories. The preferences and goals may include an indication of a user's specific exercise needs, such as an indication of a maximum exercise intensity that should not be exceeded, an indication of a maximum exercise duration that should not be exceeded, or an indication of any medically prescribed exercise restrictions that are specific to the user.

Process 900 identifies accumulated details regarding any user modifications to exercise events (step 920). The accumulated details can be identified from an associated data structure, such as observations 332 of FIG. 3. Accumulated details regarding the user modifications detail any override actions taken by the user either prior to, or during an exercise sequence. Accumulated details can include, but are not limited to, applications running at the time of the modification, peripheral and input devices in use at the time of the user modification, and calendar events occurring at the time of the user modification. Accumulated details can also include any rationale that the user has provided for modifying the exercise sequence. Override actions taken by the user can include, but are not limited to, a cancellation of the exercise sequence, a delay of the exercise sequence, a modification of the intensity of the exercise sequence, and a modification of the duration of the exercise sequence.

Process 900 identifies scheduled events (step 930). The scheduled events can be identified from an associated calendar application, such as calendar 326 of FIG. 3. The scheduled events may be, but not limited to, an upcoming teleconference or video conference, a meeting, or scheduled time during which a user will be away from the smart workstation.

Responsive to identifying preferences and goals for the exercise sequence, accumulated details regarding any user modifications to exercise events, and scheduled events, process 900 determines whether to initiate an exercise sequence on the associated smart workstation (step 940). The decision on whether to initiate an exercise sequence is based on references and goals for the exercise sequence, accumulated details regarding any user modifications to exercise events, and scheduled events that may interfere with the exercise sequence. The decision can be made by an algorithm, policy, or other logic that can apply the references and goals for the exercise sequence, accumulated details regarding any user modifications to exercise events, and scheduled events in determining whether to initiate an exercise sequence.

In an illustrative embodiment, the system, through sensors on the platform, such as in the seat or an attached treadmill, can detect whether a user is present at the workstation. Process 900 does not initiate an exercise sequence when nobody is present at the workstation. If a calendared event is scheduled to occur at a particular time, process 900 can schedule, modify, or terminate any ongoing sequence prior to the occurrence of the calendared event so that adequate time is allocated to the user to arrive at and attend the scheduled calendared event, based on for example, a calendar reminder time. Other events taking place at the workstation, such as for example, but not limited to a teleconference or video conference could be compatible with an exercise sequence as determined according to the user's preferences and goals, such as preferences/goals 328 of FIG. 3.

Responsive to determining to initiate an exercise sequence on the associated smart workstation ("yes" at step 940), process 900 initiates the exercise sequence (step 950), with the process terminating thereafter. The smart workstation is transformed from a sedentary state to an active state as described in FIG. 6 and FIG. 7 above, allowing the user to perform the exercise sequence. In an illustrative embodiment, a user can provide an acknowledgement to initiate the exercise sequence prior to process 900 initiating the exercise sequence.

The exercise event is realized by an integrated mechanism that converts the workstation from a sitting position into a standing position, and back again. The intent is to provide a seamless transition from sedentary to active state without interrupting the work event. If the user takes no action, the orchestrator activates the smart workstation which through electromechanical means, transforms itself into an exercise platform (illustrations below). The user merely has to change from sitting to standing position and begin walking/jogging (depending on intensity). Because the entire workspace has adapted to this new mode, whatever work the user is engaged in at the time can continue smoothly, without interruption. After the sequence is complete, the orchestrator tells the smart workstation to convert back to a standard workstation, and the user adopts a sitting position.

Responsive to determining not to initiate an exercise sequence on the associated smart workstation ("no" at step 940), process 900 waits for a predetermined period of time (step 960). Process 900 then iterates back to step 910 to determine whether an exercise sequence can be initiated at some subsequent time.

Figure 10:
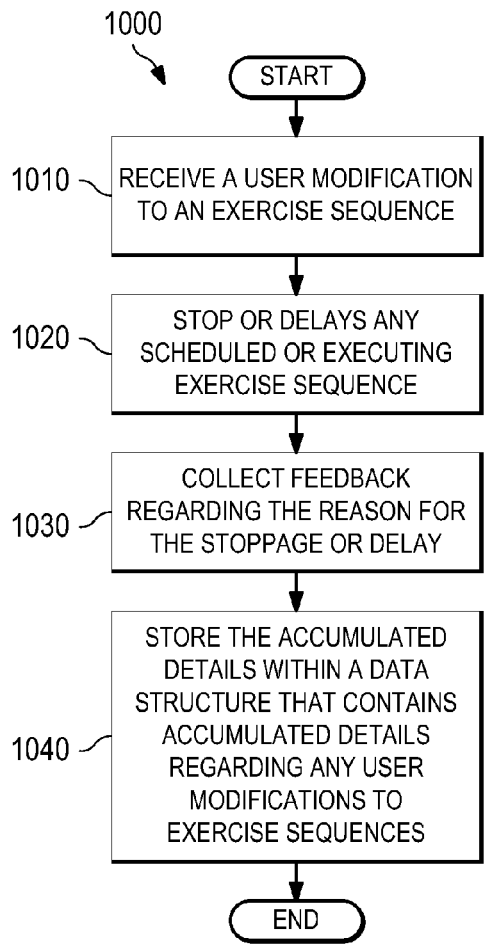
FIG. 10 is a flowchart of processing steps for recording state information and accumulated details regarding any user modifications to exercise events on the associated smart workstation according to an illustrative embodiment.

Referring now to FIG. 10, a flowchart of processing steps for recording state information and accumulated details regarding any user modifications to exercise events on the associated smart workstation is shown according to an illustrative embodiment. Process 1000 is a software process, executing on a software component, such as learning module 330 of FIG. 3.

Process 1000 begins by receiving a user modification to an exercise sequence (step 1010). The user modification details override actions taken by the user either prior to, or during an exercise sequence. The override action can include, but is not limited to, a cancellation of the exercise sequence, a delay of the exercise sequence, a modification of the intensity of the exercise sequence, and a modification of the duration of the exercise sequence. The override action can also include the use of an application or input device that is incompatible with the exercise sequence.

Responsive to receiving the override action, process 1000 stops or delays any scheduled or executing exercise sequence (step 1020). Given the stochastic nature of application and peripheral use (for example, a graphics tablet may be accessed during an in-progress exercise), process 1000 does not abruptly halt a sequence if a non-permissible state is activated; rather it prompts the user to decide whether to continue, to halt or to decrease the intensity of the event. The user response to that query is logged by the learning module into the observations database for future events. Once a threshold of exercise modification events is reached for a particular pattern, a particular rule fitting that pattern would be modified. This is valuable because the user is not always aware of their limitations, so the initial configuration may be either too aggressive or too tame.

Responsive to stopping or delaying any scheduled or executing exercise sequence, process 1000 collects feedback regarding the reason for the stoppage or delay (step 1030). This feedback forms accumulated details that can be used to modify the user's preferences and goals. Accumulated details can include, but are not limited to, applications running at the time of the modification, peripheral and input devices in use at the time of the user modification, and calendar events occurring at the time of the user modification. Accumulated details can also include any rationale that the user has provided for modifying the exercise sequence.

Responsive to collecting feedback regarding the reason for the stoppage or delay, process 1000 stores the accumulated details within a data structure that contains accumulated details regarding any user modifications to exercise sequences (step 1040), with the process terminating thereafter. The user modifications contained within the data structure detail any override actions taken by the user either prior to or during an exercise sequence. When a user makes a user modification to an exercise sequence initiated process 1000 logs current state data of the associated data processing system, including which monitored activities are currently active. These accumulated details can then be later utilized in scheduling an exercise sequence so as to minimize the probability of future user modifications.

Figure 11:
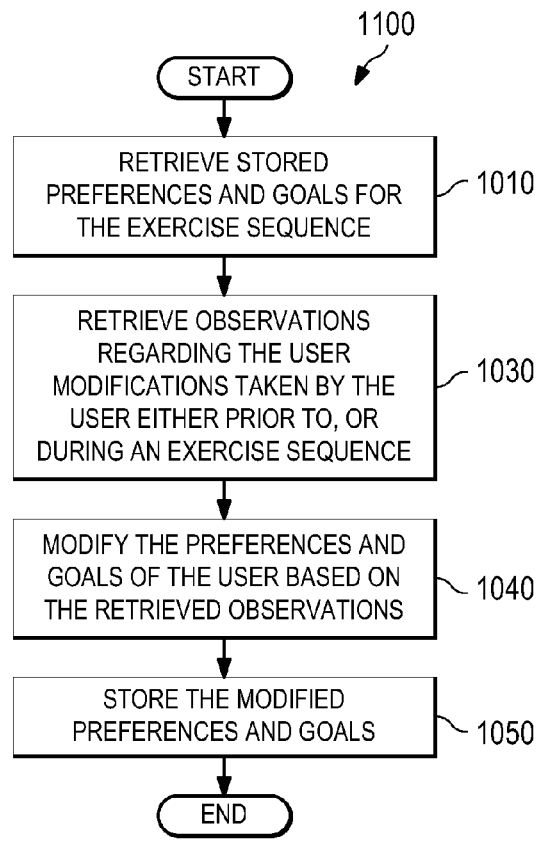
FIG. 11 is a flowchart of processing steps for maintaining user specifications about the desired exercise goals according to an illustrative embodiment.

Referring now to FIG. 11, a flowchart of processing steps for maintaining user specifications about the desired exercise goals is shown according to an illustrative embodiment. Process 1100 is a software process, executing on a software component, such as configurator 336 of FIG. 3.

Process 1100 begins by retrieving stored preferences and goals for the exercise sequence (step 1110). The stored preferences and goals can be retrieved from a data structure, such as preferences/goals 328 of FIG. 3. The preferences and goals are user specifications about the desired exercise goals. These specifications can be, for example, but not limited to, goals regarding a specific number of calories to burn during an exercise session or over a period of time, goals regarding an amount of time to exercise during an exercise session or over a period of time, goals regarding an amount of weight to lose or gain over a period of time, and goals regarding a desired target body mass index. The preferences and goals can be identified from an associated data structure, such as preferences/goals 328 of FIG. 3.

The preferences and goals may include user specifications regarding what calendar events and monitored activities are compatible with an exercise sequence. The preferences and goals may include an indication of which of monitored activities are compatible with an exercise sequence as well as a user-specified exercise intensity for a specific one of monitored activity, or for a specific calendared event. The preferences and goals may include an indication of certain times at which an exercise sequence should not be initiated. The preferences and goals may include an indication of certain calendared events that are incompatible with an exercise sequence. The preferences and goals may include an indication of a user's exercise goals that should be achieved over given period of time, for example, a predetermined period of time to exercise, or a desire to burn a certain number of calories. The preferences and goals may include an indication of a user's specific exercise needs, such as an indication of a maximum exercise intensity that should not be exceeded, an indication of a maximum exercise duration that should not be exceeded, or an indication of any medically prescribed exercise restrictions that are specific to the user.

Process 1100 then retrieves observations regarding the user modifications taken by the user either prior to or during an exercise sequence (step 1130). The observations are accumulated details that can be identified from an associated data structure, such as observations 332 of FIG. 3. Accumulated details regarding the user modifications detail any override actions taken by the user either prior to or during an exercise sequence. Accumulated details can include, but are not limited to, applications running at the time of the modification, peripheral and input devices in use at the time of the user modification, and calendar events occurring at the time of the user modification. Accumulated details can also include any rationale that the user has provided for modifying the exercise sequence. Override actions taken by the user can include, but are not limited to, a cancellation of the exercise sequence, a delay of the exercise sequence, a modification of the intensity of the exercise sequence, and a modification of the duration of the exercise sequence.

Process 1100 then modifies the preferences and goals of the user based on the retrieved observations (step 1140). Modifications to the exercise sequence through user response are logged by the learning module into the observations database for future events. Once a threshold of exercise modification events is reached for a particular pattern, a particular rule fitting that pattern would be modified. This is valuable because the user is not always aware of their limitations, so the initial configuration may be either too aggressive, or too tame.

Responsive to modifying the preferences and goals of the user based on the retrieved observations, process 1100 stores the modified preferences and goals (step 1150), with the process terminating thereafter. The modified preferences and goals are stored in a data structure, such as preferences/goals 328 of FIG. 3. The modified preferences and goals can then be utilized by the orchestrator in determining subsequent exercise sequences.

Thus, the illustrative embodiments described herein provide an exercise-integrated workstation that overcomes the drawbacks of existing methods through systematic and adaptive awareness of the user's current and projected state of work activity. The exercise-integrated workstation integrates an exercise regimen seamlessly into the work schedule without significant impact to the work being performed. The exercise-integrated workstation is realized by a software mechanism which functions in concert with an articulated workstation that is coupled to a workout device such as a treadmill. The exercise-integrated workstation takes the user from a sitting position to a standing and walking position for exercise sequences throughout the work day based on the nature of the work being performed. Through a combination of calendar access, current task awareness and user preferences, this virtual coach prescribes exercise sequences to keep the user in shape without impacting productivity. In addition, an integrated learning component correlates user overrides and modifications to the exercise recommendations to the state of the work being performed to better tune future exercise events.

The flowcharts and block diagrams in the figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method for initiating an exercise sequence of an exercise equipment communicatively coupled to a computer processor, the method comprising:

a computer processor identifying a set of monitored activities actively running in the computer processor;

the computer processor identifying a set of preferences and goals for the exercise sequence of an exercise equipment communicatively coupled to the computer processor;

the computer processor identifying a set of accumulated details regarding any user modifications to previous exercise sequences of the exercise equipment communicatively coupled to the computer processor;

the computer processor identifying a set of scheduled events;

responsive to identifying the set of monitored activities actively running in the computer processor, the set of preferences and goals, the set of accumulated details, and the set of scheduled events, the computer processor determining whether to initiate the exercise sequence of the exercise equipment;

responsive to determining to initiate the exercise sequence of the exercise equipment, the computer processor initiating the exercise sequence of the exercise equipment and activating the exercise equipment; and the computer processor causing the exercise equipment to adjust intensity of its exercise sequence after the initiating the exercise sequence equipment and while the exercise equipment is activated, the adjusting based on a type of peripheral device that is being used by a user, a type of a computer application that is actively being used by the user, and a type of user activity specified by the set of scheduled events, wherein the peripheral device is communicatively coupled to the computer processor.

2. The method of claim 1, wherein the set of monitored activities actively running in the computer processor is selected from the group consisting of execution of an email application, execution of a photo editing application, execution of a spreadsheet application, execution of a word processing application, use of a keyboard, use of a mouse, use of a graphics tablet, use of a trackpad, use of a connected telephone, and combinations thereof.

3. The method of claim 1, wherein the set of preferences and goals for the exercise sequence of the exercise equipment communicatively coupled to the computer include an indication of which of the set of monitored activities actively running in the computer processor are compatible with the exercise sequence, an indication of a user specified exercise intensity for a specific one of the set of monitored activities actively running in the computer processor, a user specified exercise intensity for a specific one of the set of scheduled event, an indication of certain times at which the exercise sequence of the exercise equipment should not be initiated, an indication of ones of the set of scheduled events that are incompatible with the exercise sequence, an indication of a user's exercise goals that should be achieved over given period of time, an indication of a user's specific exercise needs, and combinations thereof.

4. The method of claim 1, wherein the set of accumulated details is selected from the group consisting of applications running at the time of a user modification to the exercise sequence of the exercise equipment, peripheral devices in use at the time of the user modification to the exercise sequence of the exercise equipment, input devices in use at the time of the user modification to the exercise sequence of the exercise equipment, and calendar events occurring at the time of the user modification to the exercise sequence of the exercise equipment, rationale that the user has provided for modifying the exercise sequence of the exercise equipment.

5. The method of claim 1, wherein the set of scheduled events is selected from the group consisting of a teleconference, a video conference, a meeting, and a scheduled time during which the user will be away from the exercise equipment communicatively coupled to the computer.

6. The method of claim 1 further comprising:

responsive to determining to initiate the exercise sequence, the computer processor receiving a user acknowledgement to initiate the exercise sequence;

the computer processor receiving a user acknowledgement to initiate the exercise sequence, initiating the exercise sequence of the exercise equipment; and responsive to initiating the exercise sequence, the computer processor receiving a user modification to the exercise sequence of the exercise equipment.

7. The method of claim 6 further comprising:

the computer processor receiving the user modification to the exercise sequence of the exercise equipment, wherein the user modification describes at least one override action taken by the user, the override action comprising a cancellation of the exercise sequence, a delay of the exercise sequence, a modification of an intensity of the exercise sequence, a modification of a duration of the exercise sequence, and an initiation of an unscheduled user-initiated exercise sequence.

8. The method of claim 7 further comprising:

responsive to receiving the user modification to the exercise sequence of the exercise equipment, the computer processor logging the user modification to the exercise sequence in a database;

the computer processor utilizing the user modification to the exercise sequence of the exercise equipment in response to scheduling a subsequent exercise sequence to minimize a probability of subsequent user modifications; and responsive to reaching a threshold of exercise modification events for a particular one of the set of preferences and goals for the exercise sequence, the computer processor modifying the particular one of the set of preferences and goals for the exercise sequence.

* * * * *